US010151606B1

(12) United States Patent
Memarzanjany et al.

(10) Patent No.: US 10,151,606 B1
(45) Date of Patent: Dec. 11, 2018

(54) TRACKING POSITION AND MOVEMENT USING A MAGNETIC FIELD

(71) Applicant: Ommo Technologies, Inc., Plano, TX (US)

(72) Inventors: Fathollah Memarzanjany, Dallas, TX (US); Minjie Zheng, Dallas, TX (US)

(73) Assignee: Ommo Technologies, Inc., Dallas, TX (US)

( * ) Notice: Subject to any disclaimer, the term of this patent is extended or adjusted under 35 U.S.C. 154(b) by 132 days.

(21) Appl. No.: 15/436,967

(22) Filed: Feb. 20, 2017

Related U.S. Application Data

(60) Provisional application No. 62/299,185, filed on Feb. 24, 2016.

(51) Int. Cl.
| | |
|---|---|
| *G01D 5/12* | (2006.01) |
| *G01D 5/14* | (2006.01) |
| *G01D 5/20* | (2006.01) |
| *G01B 7/14* | (2006.01) |
| *G01B 7/30* | (2006.01) |
| *G01V 3/08* | (2006.01) |
| *G01V 3/10* | (2006.01) |

(52) U.S. Cl.
CPC .................. *G01D 5/2046* (2013.01)

(58) Field of Classification Search
CPC .. G01D 5/12; G01D 5/14; G01D 5/20; G01D 5/2046; G01B 7/14; G01B 7/30; G01V 3/08; G01V 3/10
See application file for complete search history.

(56) References Cited

U.S. PATENT DOCUMENTS

| | | | |
|---|---|---|---|
| 3,301,070 A | 1/1967 | Lapierre | |
| 3,868,555 A | 2/1975 | Knowles | |
| 5,153,546 A * | 10/1992 | Laskaris | ............... G01R 33/28 |
| | | | 324/318 |
| 5,453,686 A | 9/1995 | Anderson | |

(Continued)

FOREIGN PATENT DOCUMENTS

| | | |
|---|---|---|
| CN | 103412337 | 11/2013 |
| EP | 0928976 | 7/1999 |

(Continued)

OTHER PUBLICATIONS

STMicroelectronics, Digital output magnetic sensor: ultra-low-power, high-performance 3-axis magnetometer, May 2015, 33 pages.

(Continued)

*Primary Examiner* — Neel Shah
(74) *Attorney, Agent, or Firm* — Henry Patent Law Firm PLLC (57) ABSTRACT

In a general aspect, a position tracking system includes a sphere magnet that produces a magnetic field in a space. A magnetic field control system is configured to change the magnetic field by rotating the sphere magnet through a time-series of rotations over a time period. A position marker includes a magnetic field sensor that is configured to measure the magnetic field in the space during the time period. A data processing apparatus is configured to determine the position of the position marker based on magnetic field measurements obtained by the magnetic field sensor in the space during the time period.

17 Claims, 6 Drawing Sheets

(56) References Cited

U.S. PATENT DOCUMENTS

| | | | |
|---|---|---|---|
| 5,558,091 A | 9/1996 | Acker et al. | |
| 5,583,478 A | 12/1996 | Renzi | |
| 5,646,524 A | 7/1997 | Gilboa | |
| 6,049,327 A | 4/2000 | Walker et al. | |
| 6,073,043 A | 6/2000 | Schneider | |
| 6,140,813 A | 10/2000 | Sakanoue et al. | |
| 6,141,643 A | 10/2000 | Harmon | |
| 6,380,923 B1 | 4/2002 | Fukumoto et al. | |
| 6,400,139 B1 | 6/2002 | Khalfin et al. | |
| 6,420,640 B2 | 7/2002 | Koch | |
| 6,593,730 B2 | 7/2003 | Zapf | |
| 6,624,626 B2 | 9/2003 | Khalfin | |
| 6,686,881 B1 | 2/2004 | Lu et al. | |
| 6,747,632 B2 | 6/2004 | Howard | |
| 6,789,043 B1 | 9/2004 | Nelson et al. | |
| 6,830,337 B2 | 12/2004 | Angerpointner | |
| 6,861,945 B2 | 3/2005 | Kim et al. | |
| 6,967,596 B2 | 11/2005 | Nguyen | |
| 6,979,164 B2 | 12/2005 | Kramer | |
| 7,038,658 B2 | 5/2006 | Seki et al. | |
| 7,042,438 B2 | 5/2006 | McRae et al. | |
| 7,498,956 B2 | 3/2009 | Baier et al. | |
| 7,703,548 B2 | 4/2010 | Clark | |
| 7,798,253 B2 | 9/2010 | Schuh | |
| 7,859,249 B2 | 12/2010 | Zeller et al. | |
| 7,868,610 B2 | 1/2011 | Velinsky et al. | |
| 8,200,314 B2 | 6/2012 | Bladen et al. | |
| 8,208,192 B2 | 6/2012 | Keyworth et al. | |
| 8,279,091 B1 | 10/2012 | Tran et al. | |
| 8,381,718 B1 | 2/2013 | Luconi | |
| 8,425,438 B2 | 4/2013 | Fujimoto et al. | |
| 8,519,950 B2 | 4/2013 | Radivojevic et al. | |
| 8,450,997 B2 | 5/2013 | Silverman | |
| 8,473,026 B2 | 6/2013 | Ferre et al. | |
| 8,490,717 B2 | 7/2013 | Bergstrom et al. | |
| 8,525,627 B2 | 9/2013 | Higuchi | |
| 8,743,052 B1 | 6/2014 | Keller et al. | |
| 8,818,486 B2 | 8/2014 | Montag | |
| 8,903,414 B2 | 12/2014 | Marti et al. | |
| 8,955,458 B2 | 2/2015 | Salzmann et al. | |
| 9,002,675 B2 | 4/2015 | McIntyre et al. | |
| 9,182,456 B2 | 11/2015 | Shoemaker et al. | |
| 9,285,438 B2 | 3/2016 | Donovan et al. | |
| 9,551,561 B2 | 1/2017 | Kochanski | |
| 9,638,822 B2 | 5/2017 | Doany et al. | |
| 9,658,692 B1 | 5/2017 | Keyes et al. | |
| 9,823,092 B2 | 11/2017 | David et al. | |
| 2004/0107070 A1 | 6/2004 | Anderson et al. | |
| 2004/0263473 A1 | 12/2004 | Cho et al. | |
| 2006/0164086 A1* | 7/2006 | Kohlmuller | A61B 5/0555 324/307 |
| 2006/0255795 A1 | 11/2006 | Higgins et al. | |
| 2006/0293593 A1 | 12/2006 | Govari et al. | |
| 2007/0132722 A1 | 6/2007 | Kim et al. | |
| 2008/0307025 A1 | 12/2008 | Licul | |
| 2009/0054077 A1 | 2/2009 | Gauthier et al. | |
| 2009/0146947 A1 | 6/2009 | Ng | |
| 2009/0156309 A1 | 6/2009 | Weston et al. | |
| 2009/0212979 A1 | 8/2009 | Catchings et al. | |
| 2009/0322680 A1 | 12/2009 | Festa | |
| 2010/0090949 A1 | 4/2010 | Tianqiao et al. | |
| 2010/0156783 A1 | 6/2010 | Bajramovic | |
| 2010/0231505 A1 | 9/2010 | Iwata | |
| 2011/0041834 A1 | 2/2011 | Liao | |
| 2012/0053448 A1* | 3/2012 | Griswold | A61B 5/055 600/411 |
| 2012/0056805 A1 | 3/2012 | Bronner, Sr. et al. | |
| 2012/0084051 A1* | 4/2012 | Hackner | G01V 3/081 702/153 |
| 2012/0319940 A1 | 12/2012 | Bress et al. | |
| 2013/0043863 A1* | 2/2013 | Ausserlechner | G01D 5/145 324/207.2 |
| 2013/0238270 A1 | 9/2013 | Knalfin et al. | |
| 2013/0303878 A1 | 11/2013 | Nevo et al. | |
| 2014/0002063 A1 | 1/2014 | Ashe | |
| 2014/0055338 A1 | 2/2014 | Ryan | |
| 2014/0283599 A1 | 9/2014 | Kim et al. | |
| 2014/0371574 A1 | 12/2014 | Shusterman et al. | |
| 2015/0035743 A1 | 2/2015 | Rosener | |
| 2015/0061994 A1 | 3/2015 | Dai et al. | |
| 2015/0077336 A1 | 3/2015 | Elangovan | |
| 2015/0149104 A1 | 5/2015 | Baker et al. | |
| 2015/0185838 A1 | 7/2015 | Camacho-Perez et al. | |
| 2015/0185852 A1 | 7/2015 | Guo | |
| 2015/0198464 A1 | 7/2015 | El Alami | |
| 2015/0241976 A1 | 8/2015 | Zhao et al. | |
| 2015/0253847 A1 | 9/2015 | Harris et al. | |
| 2016/0011285 A1* | 1/2016 | Griswold | A61B 5/7475 600/411 |
| 2016/0223577 A1 | 8/2016 | Klosinski et al. | |
| 2017/0176623 A1* | 6/2017 | Appleby | G01V 3/104 |
| 2018/0000554 A1 | 1/2018 | Paradis et al. | |

FOREIGN PATENT DOCUMENTS

| | | |
|---|---|---|
| EP | 1413820 | 4/2004 |
| WO | 2014/027243 | 2/2014 |
| WO | 2016/041088 | 3/2016 |
| WO | 2017/139871 | 8/2017 |

OTHER PUBLICATIONS

Paperno, E., et al., A new method for magnetic position and orientation tracking, IEEE Transactions on Magnetics, vol. 37, No. 4, Jul. 2001, 3 pages.

Fang, W., et al., Optimization of Measuring Magnetic Fields for Position and Orientation Tracking, IEEE/ASME: Transactions on Mechatronics, vol. 16, No. 3, Jun. 2011, 9 pages.

Raab, F H., et al., Magnetic Position and Orientation Tracking System, IEEE Transactions on Aerospace and Electronic Systems, vol. AES-15, No. 5, Sep. 1979, 10 pages.

Schlageter, V., et al., A Magnetic Tracking System based on Highly Sensitive Integrated Hall Sensors, JSME International Journal, Series C, vol. 45, No. 4, 2002, 7 pages.

Godinez, F. A., et al., Note: Design of a novel rotating magnetic field device, Rev. Sci. Instrum. 83, 066109, 2012, 4 pages.

USPTO, Restriction Requirement dated Aug. 31, 2018, in U.S. Appl. No. 15/996,055, 6 pgs.

Chen , et al., "Finexus: Tracking Precise Motions of Multiple Fingertips Using Magnetic Sensing", Univ of Washington, UbiComp Lab, May 2016, 11 pgs.

Popek , et al., "Localization Method for a Magnetic Capsule Endoscope Propelled by a Rotating Magnetic Dipole Field", IEEE International Conference on Robotics and Automation, Karlsruhe, Germany, May 2013, 6 pgs.

Schultze , et al., "Unambiguous position and orientation tracking using a rotating magnet", Journal of Applied Physics 114, 114502, 2013, 12 pgs.

Song , et al., "6-D Magnetic Localization and Orientation Method for an Annular Magnet Based on a Closed-Form Analytical Model", IEEE Transactions on Magnetics, vol. 50, No. 9, Sep. 2014, 11 pgs.

Song , et al., "An Electromagnetic Localization and Orientation Method Based on Rotating Magnetic Dipole", IEEE Transactions on Magnetics, Mar. 2013, 5 pgs.

Strachen , et al., "Accurate Indoor Navigation with Spinning Magnets", Dept of Electrical and Computer Engineering, Univ of Wisconsin-Madison, Apr. 2018, 2 pgs.

Wang , et al., "Analysis and visualization of rotation searching efficiency in two-round rotation based magnetic tracking", Dept. of Electronic Engineering, Fudan University, Shanghai, China, Nov. 18, 2015, 13 pgs.

\* cited by examiner

TRACKING POSITION AND MOVEMENT USING A MAGNETIC FIELD

CROSS-REFERENCE TO RELATED APPLICATIONS

This application claim priority to U.S. Provisional Application No. 62/299,185, filed Feb. 24, 2016 and entitled "Tracking Position and Movement Using a Magnetic Field," which is hereby incorporated by reference.

BACKGROUND

The following description relates to using a magnetic field to track position and movement.

Some existing systems can detect the position or movement of an object based on data collected by sensors. For example, vision-based positioning systems operate in the optical frequency range and utilize a line of sight between the image sensor and the object. As another example, sound-based positioning systems operate in an acoustic frequency range and utilize a propagation medium between the acoustic sensor and the object. As another example, inertial-based systems can use accelerometers or gyroscopes, for instance, to detect certain types of movement.

DETAILED DESCRIPTION

In some aspects of what is described here, the positions of objects are tracked using a time-varying magnetic field. In some examples, the positions of known markers relative to a reference point are determined (e.g., with millimeter precision), without line-of-sight. In some implementations, a mobile and low power position tracking system is used for tracking small, refined movements in a volume (such as, for example, movements of fingers and hands). In some cases, tracking the motions of fingers and hands provides useful and intuitive forms of input such as, for example, manipulating 3D digital interfaces with a user's hands (e.g., in an augmented reality or virtual reality system), providing input through a virtual trackpad on any surface (e.g., operating as a two-dimensional or three-dimensional mouse), providing complex gesture input to control electronic devices and others. In some cases, these and other useful forms of input can be provided by tracking body parts, digits, clothing, accessories, etc., or by tracking other types of objects that are not part of or associated with a body. In some cases, a skeletal model can be constructed, movement of a system (e.g., a biological system, industrial system, etc.) can be tracked over time, or other types of information can be obtained based on the position information.

In some instances, the subject matter described here can be implemented in a manner that provides technical advantages. For example, a position tracking system can operate on low power, for instance, by using small coils to align a sphere magnet. As another example, a position tracking system can be implemented using small components (e.g., millimeter-size components, or another size), for instance, to provide a mobile and wearable system. In some cases, position can be detected in three-dimensions without requiring line-of-sight, and millimeter-scale positional precision can be achieved (e.g., by reducing or eliminating noise amplification). In some instances, a position tracking system can operate independent of lighting conditions or other environmental factors. In some implementations, a small sphere magnet can be used with small coils to quickly and precisely generate a specific magnetic field configuration at high speed. For example, the sphere magnet may be rotated at a speed of 1 kiloHertz (kHz) or another speed (faster or slower) to achieve position measurements with millimeter-level precision. In some implementations, the sphere magnet and coil configuration can limit distortion and obtain measurements with a desired precision and speed, without the need to calibrate beforehand.

In some aspects of the subject matter described here, a position tracking system includes one or more controllable magnetic field generators, a control system to control the magnetic field, one or more magnetic field sensors and a data processing unit. The controllable magnetic field generator can include, for example, multidimensional fixed magnets (e.g., sphere magnets or other types of magnets) that are controlled by circuits, spinning magnets, pulser magnets, etc. The control system can control the magnetic field precisely, for example, using a sphere magnet, pulser magnets, magnets mounted on motors, or other types of magnet systems. In the example of a sphere magnet, the sphere magnet can be surrounded by small coils that align the magnet's poles with the activated coils, in some cases, on a sub-millisecond time-scale. The magnetic field sensors can be 3-axis magnetic field sensors such as, for example, magnetometer, GMR sensors, AMR sensors, hall-effect sensors, or another type of magnetic field sensor. The position tracking system can also include a power supply or power source.

In some implementations, a position tracking system can be used in a number of applications and constructed with various form factors. As an example, a main processing unit and reference unit can be housed in an enclosure worn on the back of a user's hand or wrist, and markers can be worn on the digits to track finger movements. As another example, a main processing unit and reference unit can be housed in an enclosure worn on the body or belt, and markers can be worn on digits and limbs to track full body motion. As another example, a main processing unit and reference unit can be housed in an enclosure placed on a surface, and markers can be worn on digits and/or limbs to track full body motion. Other applications and form factors may be used.

Figure 1:
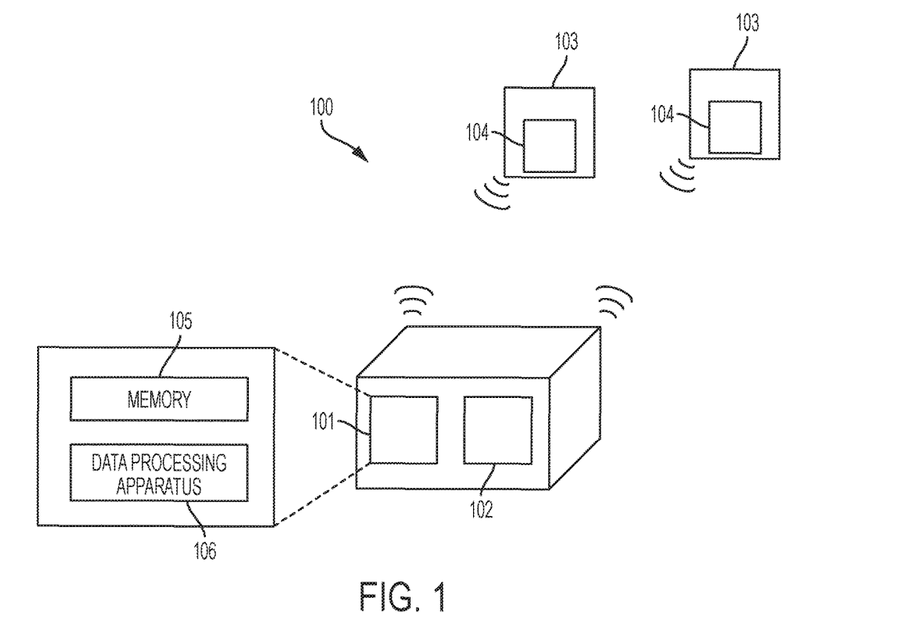
FIG. 1 is a schematic diagram showing components of an example position tracking system.

FIG. 1 is a schematic diagram showing components of an example position tracking system 100. The example position tracking system 100 shown in FIG. 1 includes a main processing unit 101, a magnetic field generator 102 and multiple position markers 103. In the example shown, the main processing unit 101 includes a memory 105 and a data processing apparatus 106, and the main processing unit 101 is housed (e.g., in a common assembly or enclosure) with the magnetic field generator 102. The main processing unit 101, the magnetic field generator 102 and the position markers 103 can each include a power source (e.g., a battery, etc.) or a connection to a power source (e.g., or a wired connection to a power supply). Each position marker 103 includes a respective magnetic field sensor 104. A position tracking system may include additional or different components, and the components may be configured as shown or they may be configured in another manner.

In the example shown in FIG. 1, the magnetic field generator 102 operates as a reference, and the position markers 103 operate as markers in the magnetic field. The example magnetic field generator 102 is a controllable system that includes a mounted, free rotating sphere magnet. The sphere magnet can be on the order of millimeters in diameter, in some cases. The sphere magnet is controlled by a magnetic field control system. The magnetic field control system can include electromagnetic coils (e.g., conductive windings) oriented along mutually-perpendicular axes of the sphere magnet. In some cases, a single coil is oriented along each Cartesian axis, or multiple coils may be oriented on one or more of the axes. In some implementations, the magnetic field generator 102 can include the example sphere magnet 202 shown in FIG. 2, and the magnetic field control system can include the example coils 204 shown in FIG. 2. The magnetic field generator 102 may be implemented or controlled using other types of components.

In some implementations, the magnetic field generator 102 and the position markers 103 contain other types of sensors, such as, for example, accelerometers or gyroscopes (or both). For example, in some cases, the orientations of the magnetic field generator 102 and each position marker 103 can be estimated based on data from accelerometers and gyroscopes. In some instances, the estimated orientations can then be used to obtain more precise position and orientation data, for example, by calculating the orientation differences between each position marker 103 and the magnetic field generator 102 and using them to refine magnetic-based measurements.

In the example shown in FIG. 1, the main processing unit 101 controls the current through the coils of the magnetic field control system to modify a magnetic field in the environment of the magnetic field generator 102. The main processing unit 101 also communicates with the position markers 103 (e.g., through a wired or wireless communication link) and processes data received from the position markers 103. The example position markers 103 each include a 3-axis magnetic field sensor 104 that senses the strength of the magnetic field along three orthogonal axes. The position markers 103 may also include a processing unit, for instance, in cases where the markers are implemented as wireless components.

In an example implementation, the position markers 103 each have an overall size in the range of 5-15 millimeters (e.g., in the longest dimension), and the magnetic field sensors 104 are digital-output magnetometers. For instance, the magnetic field sensors 104 may be implemented using the LIS3MDL model ultra-low-power, high-performance 3-axis magnetometer available from STMicroelectronics or another type of magnetometer. In some examples, the magnetic field sensors 104 can obtain magnetic field measurements with a precision of approximately 6,842 LSB/gauss for magnetic field strengths in the range of −16 to 16 gauss. The magnetic field sensors 104 may have another (higher or lower) precision and may operate in another range of magnetic field strengths. The position markers 103 can digitize, format or otherwise process the magnetic field measurements and communicate the magnetic field measurements to the main processing unit 101. In some cases, the magnetic field measurements are communicated over a wireless communication link such as, for example, Bluetooth, Wi-Fi or another wireless communication standard.

Figure 2:
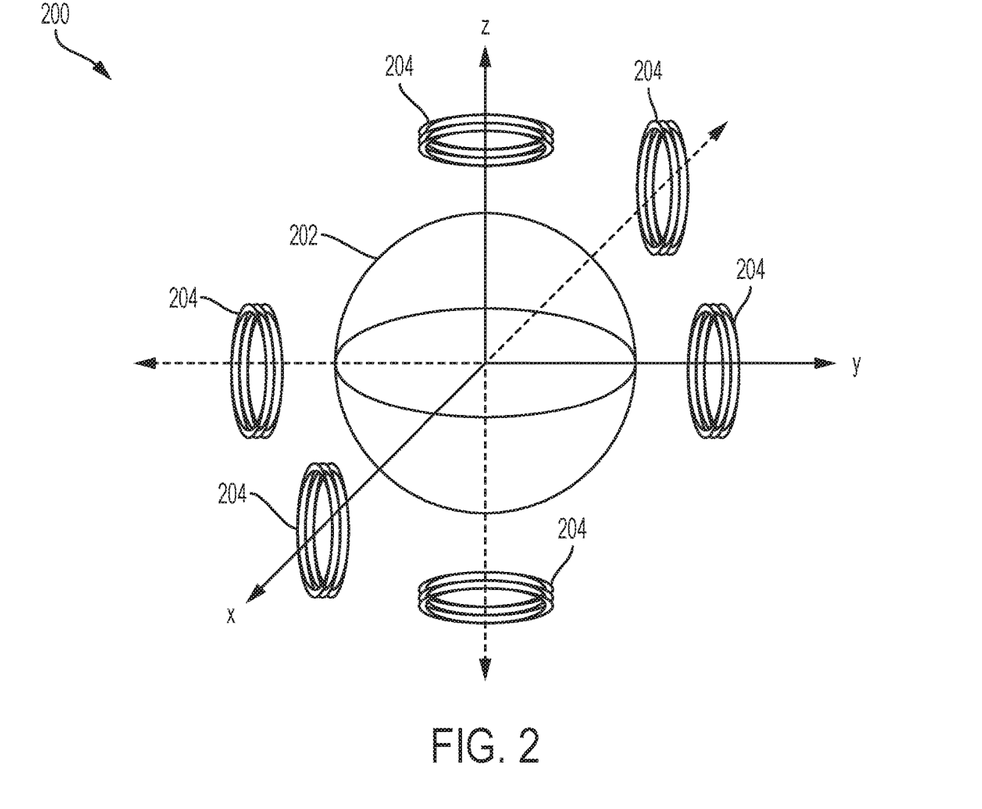
FIG. 2 is a schematic diagram showing an example magnetic field control system with a sphere magnet.

FIG. 2 is a schematic diagram showing an example magnetic field control system 200 with a sphere magnet 202. The example magnetic field control system 200 shown in FIG. 2 includes coils 204 about the sphere magnet 202. In the example shown, there are six coils 204, and each coil 204 is arranged on a respective side of the sphere magnet 202. As shown in FIG. 2, the coils 204 are aligned with the Cartesian axes defined by the coordinate system of the sphere magnet 202. In particular, one pair of the coils 204 are aligned on opposite sides of the sphere magnet 202 along the x-axis; one pair of the coils 204 are aligned on opposite sides of the sphere magnet 202 along the y-axis; and one pair of the coils 204 are aligned on opposite sides of the sphere magnet 202 along the z-axis. In some implementations, the example magnetic field control system 200 can have a different number of coils, for instance, three coils with one coil along each axis (rather than two along each axis as shown in FIG. 2). In some cases, operating additional coils can increase precision or speed, and operating fewer coils can decrease power and space consumption. A magnetic field control system may include additional or different components, and the components may be configured as shown or they may be configured in another manner.

In an example implementation, the sphere magnet 202 is a spherically-shaped permanent magnet made of Neodymium N42 grade material, having a diameter in the range of 0.5 to 1.5 inches and a maximum magnetic field strength in the range of 0.5 to 1.5 Tesla. A sphere magnet having another size, shape or maximum field strength may be used. An example Neodymium N42 grade sphere magnet has a 1 inch diameter, produces a 1 Tesla maximum field strength and provides a position tracking range of approximately 1 meter. The spherical shape of the sphere magnet 202 allows the sphere magnet 202 to be rotated by the coils 204. In some examples, the coils 204 are conductive windings (e.g., windings made of copper wire or another type of conductor) having a diameter that is approximately ¼ (one fourth) the diameter of the sphere magnet. Each conductive winding can include a number of turns that form a cylindrically-shaped or ring-shaped coil about a central axis. The coils 204 are configured (e.g., by their respective positions and orientations relative to the sphere magnet) to rotate the sphere magnet. For instance, the central axis of each coil can be aligned with a principal axis of the sphere magnet, as shown in FIG. 2.

Figure 3:
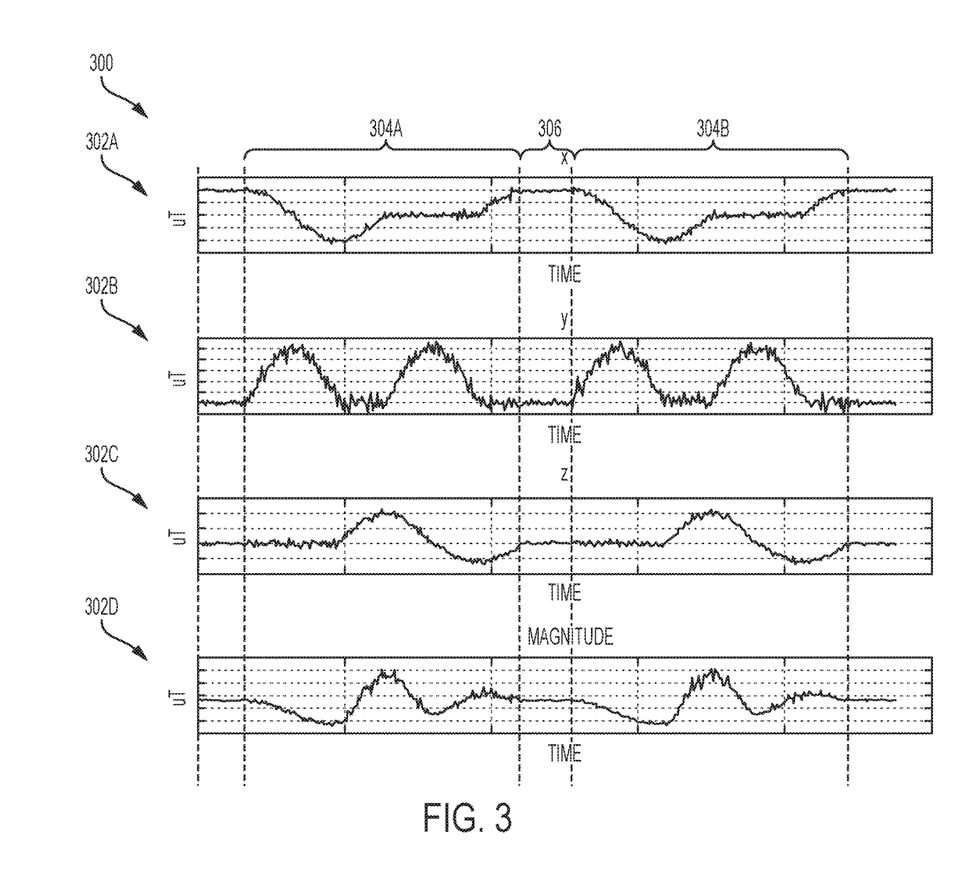
FIG. 3 is a plot showing simulated example magnetic field measurements.
Figure 4:
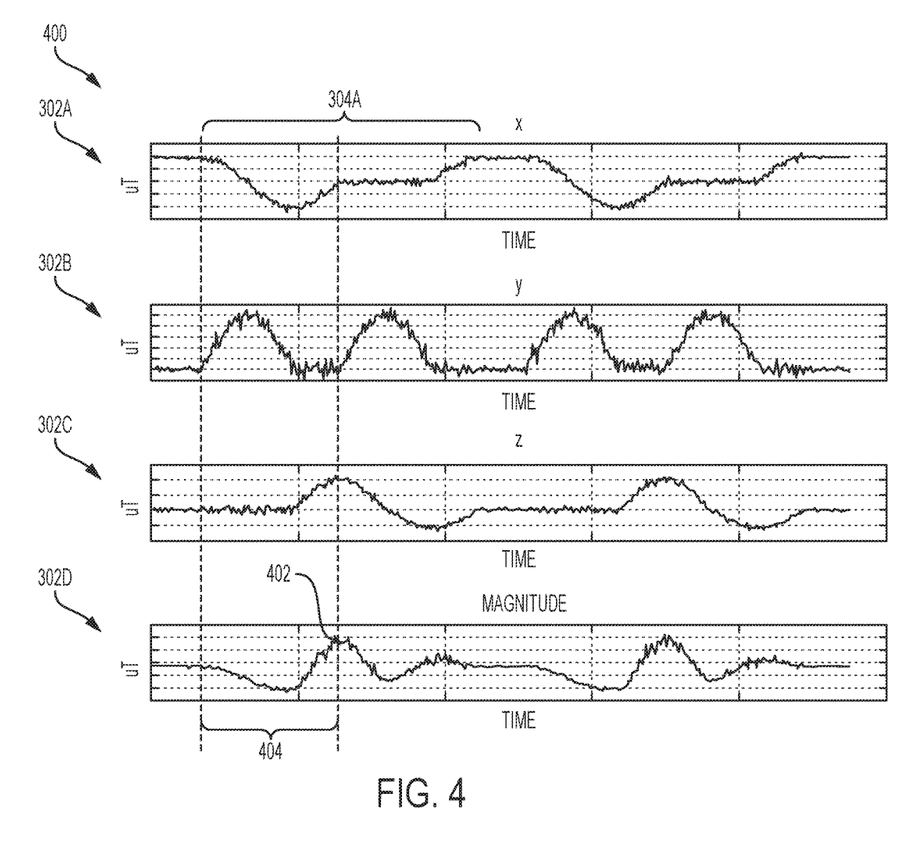
FIG. 4 is a plot showing analysis of a portion of the simulated example magnetic field measurements shown in FIG. 3.

In some aspects of operation, the position tracking system 100 shown in FIG. 1 can determine the three-dimensional positions of the position markers 103 relative to the magnetic field generator 102. In an example process described here, the position tracking system 100 shown in FIG. 1 includes the example components shown in FIG. 2. For instance, the coils 204 can rotate the sphere magnet through a time-series of rotations; the magnetic field sensors 104 can sense the magnetic field produced by the sphere magnet 202 during the time period; the data processing apparatus 106 can receive magnetic field measurements obtained by the magnetic field sensors 104; the data processing apparatus 106 can compute the three-dimensional spatial coordinates of each respective position marker 103 based on the magnetic field measurements; and the magnetic field measurements, position data and other information can be stored in and accessed from the memory 105. The process described with respect to FIGS. 3 and 4 or another type of process can be used to determine the position of a position markers 103 based on the magnetic field measurements. FIG. 3 is a plot 300 showing simulated example magnetic field measurements from the example process, and FIG. 4 is another plot 400 showing analysis of a portion of the simulated example magnetic field measurements shown in FIG. 3.

In the example process, the coils 204 along each axis are activated in quick succession, which causes the poles of the sphere magnet 202 to vibrate in a known three-dimensional motion. The known three-dimensional motion can be, for instance, a series of rotations or other types of movements. As an example, the motion can be a time-series of rotations such as, for example: a 180 degree rotation about a first axis (e.g., the z-axis), a 90 degree counter-clockwise rotation about a second axis (e.g., the y-axis) that is orthogonal to the first axis, a 180 degree about a third axis (e.g., the x-axis) that is orthogonal to the first and second axes, followed by a 90 degree clock-wise rotation about the second axis. Another time-series of rotations can be used. As another example, the motion can be one or more rotations about two different axes concurrently at different rotation speeds about each axis, for instance, executing multiple (e.g., 5, 10, 15, etc.) complete rotations about one axis while concurrently executing a different number of complete rotations (e.g., a single rotation) about a different axis. Between each magnet rotation or set of rotations, a small period of no movement (a "quiet period") may occur while the magnet is at rest. Each position marker's magnetic field sensor measures a waveform corresponding to the strength and direction of the magnetic field during each motion and the quiet periods during time intervals between the motions.

In some implementations, the magnetic field control system 200 rotates the sphere magnet 202 through a time-series of rotations and holds the sphere magnet 202 fixed (in a static orientation) during time intervals between rotations. For instance, the time-series of rotations can be executed over a time period on the order of milliseconds, seconds, minutes or longer, with each rotation having a rotation time in the range of 5 to 20 milliseconds (ms), and each time interval (between sequential rotations) having a static time in the range of 1 to 4 milliseconds (ms). In some instances, the static time intervals last approximately ⅕ (one fifth) the duration of an adjacent rotation period. The time-series of rotations may include rotations at other speeds (faster or slower) and static times of other durations (longer or shorter). In some cases, the time-series of rotations continues indefinitely, for example, repeatedly or continuously until a terminating condition is reached.

FIG. 3 is a plot 300 showing simulated example magnetic field measurements 302A, 302B, 302C, 302D. The magnetic field measurements shown in FIG. 3 represent computer simulations of measurements along three orthogonal coordinate axes by a single magnetic field sensor over the time period shown. The horizontal axis of each panel in the plot 300 represents a time period of 13 milliseconds (ms), and the vertical axis of each panel in the plot 300 represents magnetic field strength values over a range of 6 microTesla (µT).

The top panel in FIG. 3 shows a simulated measurement 302A of the magnetic field strength measured along the x-axis ($B_x$), the second panel in FIG. 3 shows a simulated measurement 302B of the magnetic field strength measured along the y-axis ($B_y$), the third panel in FIG. 3 shows a simulated measurement 302C of the magnetic field strength measured along the z-axis ($B_z$), and the bottom panel in FIG. 3 shows the simulated measurement 302D of the overall magnitude of the magnetic field $(B_x^2+B_y^2+B_z^2)^{1/2}$, which can be computed from the other simulated measurements.

The example magnetic field measurements in FIG. 3 were measured during a first time period 304A when the reference magnet is rotating, a "quiet period" 306 when the reference magnet is held in a static orientation (a time interval when the reference magnet is not rotating), and a second time period 304B when the reference magnet is rotating again. Quiet periods during time intervals between rotations can be used to sync the start and finish of each motion (e.g., without the use of synchronized clocks, etc.). The measurements from a magnetic field sensor 104 can be analyzed to find where the waveform reaches maximum and minimum on all 3 axes of the magnetic field sensor.

The plot 400 shown in FIG. 4 represents an example analysis of the simulated magnetic field measurements 302A, 302B, 302C, 302D shown in FIG. 3. In particular, FIG. 4 shows an example analysis of the waveform measured during the first period 304A shown in FIG. 3. In the example shown, the vector of the pole of the sphere magnet can be determined, for example, by using the difference between start time (marked by the end of a quiet period) and the time when the magnetic field sensor reads the maximum magnetic field value. As shown in FIG. 4, a quiet period (before the first time period 304A) is initially identified as a plateau (or flat region) in the magnetic field measurements, and a time duration 404 is measured between the end of the quiet period and a maximum 402 of the waveform during the first time period 304A. The difference between maximum and minimum of the measured waveform can be used to calculate the magnetic field strength at the sensor. Using the difference can reduce or remove magnetic interference, for example, interference at a different frequency than the rotation motion of the sphere magnet. The magnetic field strength can then be used to calculate the distance of the sensor from the source. The vector of the sphere magnet can be combined with the distance to yield the 3D position of the sensor in relation to the reference magnet. The measurements can be analyzed, and the position can be detected in another manner in some cases.

In the example shown in FIG. 4, the vector of the reference magnet can be determined based on the magnetic field measurements. For example, the time duration 404 can be measured from the start of motion to time of the absolute maximum field strength (in this example, the time of the largest vector magnitude combining all three axis measurements). Because the motion of rotation of the reference magnet is known, and the time taken to complete one full motion is also known, the measured time period t can be used to calculate the vector of the poles of the reference magnet. In an example, the reference magnet initially points north, then moves 190 degrees clockwise about the z-axis, then moves 190 degrees counterclockwise in a time period of 5 milliseconds (ms); if the measured time period t is 2 ms, then the north pole of the reference magnet is 152 (2/2.5*190) degrees clockwise from its original position at the time of the peak field strength. The vector of the reference magnet can be determined in another manner in some cases.

Figure 5A:
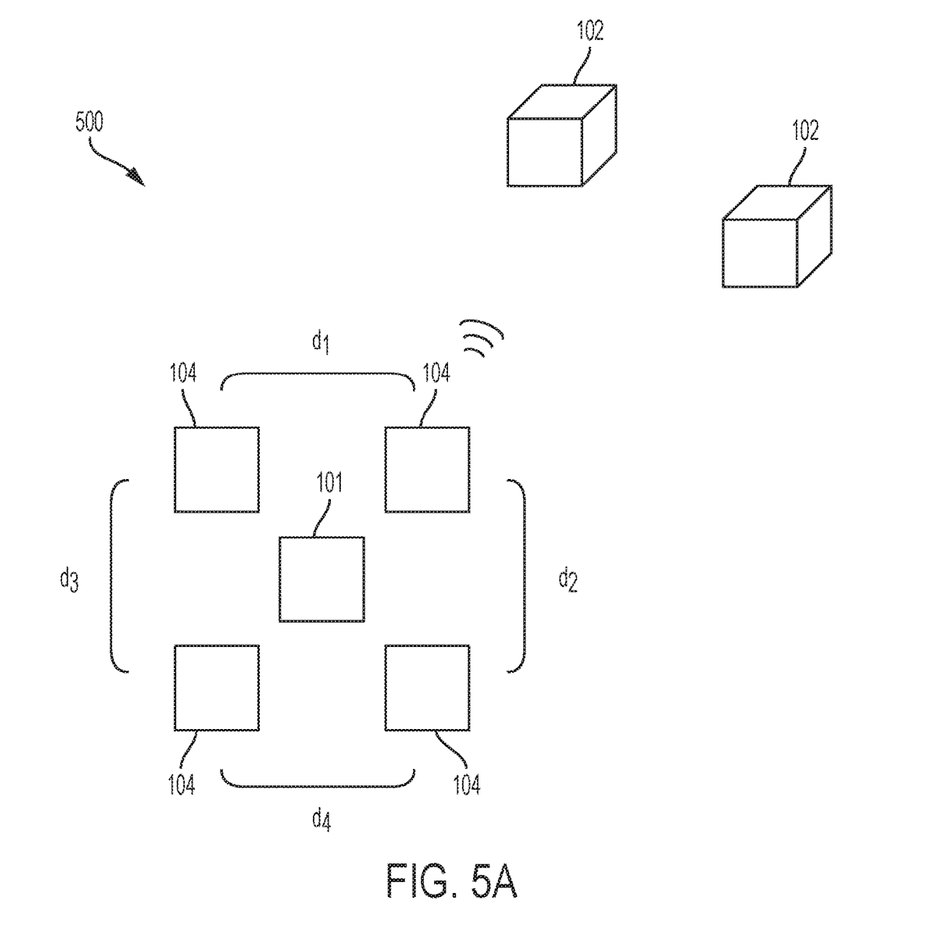
FIG. 5A is a schematic diagram showing components of an example position tracking system.
Figure 5B:
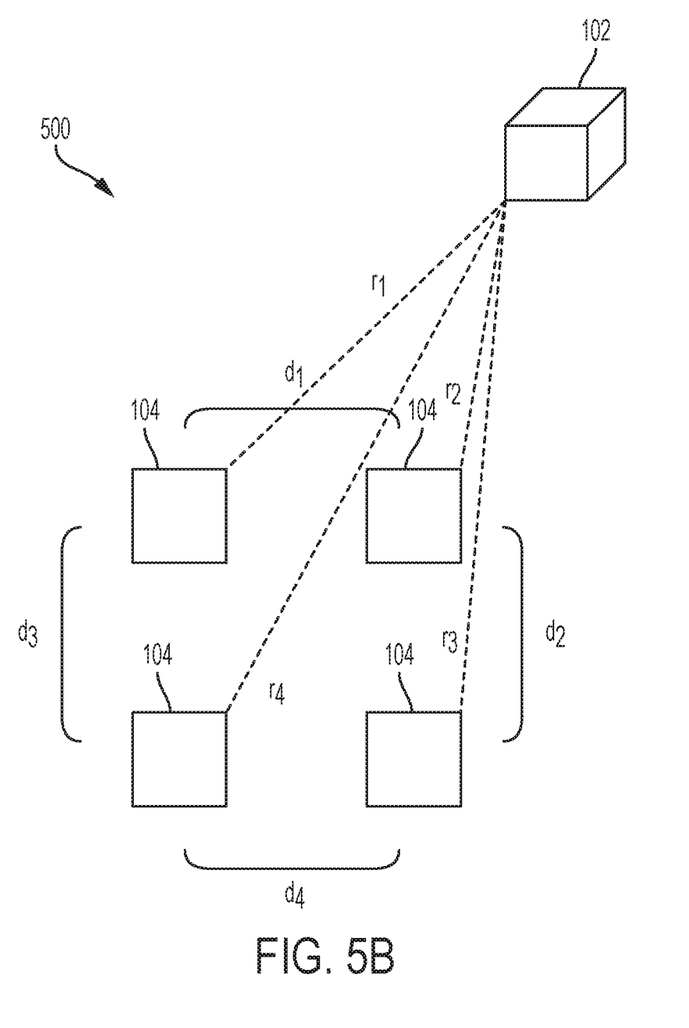
FIG. 5B is a schematic diagram showing example measurement analysis in the example position tracking system 500 shown in FIG. 5A.

FIG. 5A is a schematic diagram of an example position tracking system 500. FIG. 5B is a schematic diagram showing example measurement analysis in the example position tracking system 500. In the example position tracking system 500 shown in FIGS. 5A and 5B, the magnetic field sensors 104 are used as a reference, and the magnetic field generators 102 are used as position markers. The example position tracking system 500 shown in FIG. 5A includes a main processing unit 101, two magnetic field generators 102 and multiple magnetic field sensors 104.

Some aspects of the main processing unit 101, the magnetic field generators 102 and the magnetic field sensors 104 may be implemented as described with respect FIGS. 1 and 2, or they may be implemented in another manner, for example, as described below. A position tracking system may include additional or different components, and the components may be configured as shown or they may be configured in another manner.

In the example shown in FIG. 5A, at least three magnetic field sensors 104 are placed with known orientations and known distances from each other, for example, on a single PCB or other substrate or structure. In the example shown, the neighboring pairs of magnetic field sensors are separated by respective distances $d_1$, $d_2$, $d_3$, and $d_4$. In some instances, adding additional sensors increases certainty of marker locations. The example main processing unit 101 gathers data from the magnetic field sensors 104 and communicates with the magnetic field generators 102 (e.g., through a wired or wireless communication link). The magnetic field generators 102, which operate as markers in this example, each include a controllable magnetic field generator. The magnetic field generators 102 may each also include a processing unit, for example, if the marker is implemented as a wireless component.

In some aspects of operation, the positions of position markers containing the magnetic field generators 102 can be determined. In an example process, the controllable magnets in the magnetic field generators 102 are activated in succession by the main processing unit 101. For example, the main processing unit 101 may broadcast a message to start the motion of each position marker, or the main processing unit 101 may control them directly (e.g., through a wired connection). As an example, the motion can be: a 180 degree rotation about the z-axis, a 90 degree counter-clockwise rotation about the y-axis, a 180 degree about the x-axis, followed by a 90 degree clock-wise rotation about the y-axis. In some implementations, the timeframe of movements of each marker is mutually exclusive of the time frame of movements of the other markers, for instance, to reduce or remove magnetic interference from outside of the system. During each marker's motion, each of the magnetic field sensors 104 at the reference measures the 3-axis magnetic field vector waveform. The difference between maximum and minimum of the measured waveforms can be used to calculate the magnetic field strength at each magnetic field sensor. In some cases, using the difference reduces or removes magnetic interference at a different frequency than the rotation motion of the magnetic field generator 102. The magnetic field strength can be calculated at each sensor to determine the distance of the marker from each sensor. The calculated distance r from one sensor gives the possible locations of the marker as a sphere with radius r centered at the sensor. Since the distances between each sensor are known, multilateration approximation can be used to calculate the intersection between the spheres centered at the magnetic field sensors. The intersection can be the three-dimensional position of the active marker relative to the reference.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer storage medium for execution by, or to control the operation of, data-processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data-processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random-access memory or both. A computer can include a processor that performs actions in accordance with instructions, and one or more memory devices that store the instructions and data. A computer may also include, or be operatively coupled to receive data from or transfer data to, or both, one or more mass storage devices for storing data, e.g., magnetic disks, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. In some cases, the processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

Moreover, the separation of various system components in the implementations described above should not be understood as requiring such separation in all implementations, and it should be understood that the described program components and systems can generally be integrated together in a single product or packaged into multiple products.

A number of implementations have been described. Nevertheless, it will be understood that various modifications can be made. Accordingly, other implementations are within the scope of the following claims.

What is claimed is:

1. A position tracking system comprising:
   a sphere magnet that produces a magnetic field in a space;
   a magnetic field control system configured to change the magnetic field by rotating the sphere magnet through a plurality of rotations over a time period, wherein the magnetic field control system comprises a plurality of coils configured to rotate the sphere magnet, the plurality of coils comprising:
      a first pair of coils aligned, along a first axis, on first and second opposite sides of the sphere magnet;
      a second pair of coils aligned, along a second axis that is orthogonal to the first axis, on third and fourth opposite sides of the sphere magnet; and
      a third pair of coils aligned, along a third axis that is orthogonal to the first and second axes, on fifth and sixth opposite sides of the sphere magnet;
   a position marker comprising a magnetic field sensor configured to measure the magnetic field in the space during the time period; and
   a data processing apparatus configured to determine a position of the position marker based on magnetic field measurements obtained by the magnetic field sensor in the space during the time period.

2. The position tracking system of claim 1, wherein the magnetic field control system is configured to:
   change the magnetic field by rotating the sphere magnet through a time-series of rotations over the time period; and
   hold the sphere magnet in static orientations during time intervals between rotations in the time-series of rotations.

3. The position tracking system of claim 2, wherein determining the position of the position marker comprises identifying, from the magnetic field measurements, the time intervals between the rotations.

4. The position tracking system of claim 2, wherein rotating the sphere magnet through the time-series of rotations comprises:
   rotating the sphere magnet by 180 degrees about a first axis;
   rotating the sphere magnet by 90 degrees in a clockwise direction about a second axis that is orthogonal to the first axis;
   rotating the sphere magnet by 180 degrees about a third axis that is orthogonal to the first and second axes; and
   rotating the sphere magnet by 90 degrees in a counter-clockwise direction about the second axis.

5. The position tracking system of claim 1, wherein rotating the sphere magnet comprises activating the plurality of coils in succession.

6. The position tracking system of claim 1, wherein the magnetic field sensor is configured to measure the strength of the magnetic field along three orthogonal axes, and the data processing apparatus is configured to determine the position of the position marker with millimeter-scale precision.

7. The position tracking system of claim 6, wherein the magnetic field control system is configured to rotate the magnetic field by at least 180 degrees in a rotation time of less than 10 milliseconds, and the magnetic field sensor is configured to obtain multiple magnetic field measurements during the rotation time.

8. The position tracking system of claim 1, comprising multiple position markers each comprising a respective magnetic field sensor configured to measure the magnetic field in the space during the time period, wherein the data processing apparatus is configured to determine the respective positions of the position markers based on magnetic field measurements obtained by the respective magnetic field sensors in the space during the time period.

9. The position tracking system of claim 1, wherein the position marker is a wireless device that includes a power source.

10. The position tracking system of claim 9, comprising a main processing unit that includes the data processing apparatus, wherein the main processing unit is configured to communicate with the position markers through a wireless communication link.

11. A position tracking method comprising:

by operation of a magnetic field control system, changing a magnetic field in a space by rotating a sphere magnet through a plurality of rotations over a time period, wherein the magnetic field control system comprises a plurality of coils configured to rotate the sphere magnet, and the plurality of coils comprises:
- a first pair of coils aligned, along a first axis, on first and second opposite sides of the sphere magnet;
- a second pair of coils aligned, along a second axis that is orthogonal to the first axis, on third and fourth opposite sides of the sphere magnet; and
- a third pair of coils aligned, along a third axis that is orthogonal to the first and second axes, on fifth and sixth opposite sides of the sphere magnet;

obtaining, during the time period, magnetic field measurements at a position marker comprising a magnetic field sensor in the space;

receiving the magnetic field measurements at a data processing apparatus; and by operation of the data processing apparatus, determining a position of the position marker based on the magnetic field measurements.

12. The position tracking method of claim 11, comprising:

changing the magnetic field by rotating the sphere magnet through a time-series of rotations over the time period; and maintaining the sphere magnet in a static orientation during a time interval between two sequential rotations in the time-series of rotations.

13. The position tracking method of claim 12, wherein determining the position comprises identifying, from the magnetic field measurements, the time interval between the rotations.

14. The position tracking method of claim 12, wherein rotating the sphere magnet through the time-series of rotations comprises:

- rotating the sphere magnet by 180 degrees about a first axis;
- rotating the sphere magnet by 90 degrees in a clockwise direction about a second axis that is orthogonal to the first axis;
- rotating the sphere magnet by 180 degrees about a third axis that is orthogonal to the first and second axes; and
- rotating the sphere magnet by 90 degrees in a counter-clockwise direction about the second axis.

15. The position tracking method of claim 11, wherein rotating the sphere magnet comprises controlling current through the plurality of coils.

16. The position tracking method of claim 11, wherein rotating the sphere magnet comprises activating the plurality of coils in succession.

17. The position tracking method of claim 11, comprising, at a main processing unit comprising the data processing apparatus, receiving the magnetic field measurements from the position marker through a wireless communication link.

\* \* \* \* \*